US012564472B2

(12) United States Patent
Fontaine et al.

(10) Patent No.: US 12,564,472 B2
(45) Date of Patent: Mar. 3, 2026

(54) SYSTEM FOR GUIDING AN OSTEOTOMY PROCEDURE

(71) Applicant: KYNISKA ROBOTICS, Saint-Martin-D'Héres (FR)

(72) Inventors: Sylvain Fontaine, Saint-Martin-D'Héres (FR); Thomas Lonjaret, Saint-Martin-D'Héres (FR); Marie-Anne Chanrion, Saint-Martin-D'Héres (FR)

(73) Assignee: OSTESYS, Saint Martin d'Heres (FR)

( * ) Notice: Subject to any disclaimer, the term of this patent is extended or adjusted under 35 U.S.C. 154(b) by 124 days.

(21) Appl. No.: 18/684,715

(22) PCT Filed: Aug. 23, 2022

(86) PCT No.: PCT/EP2022/073489
§ 371 (c)(1),
(2) Date: Feb. 19, 2024

(87) PCT Pub. No.: WO2023/025807
PCT Pub. Date: Mar. 2, 2023

(65) Prior Publication Data
US 2024/0374342 A1 Nov. 14, 2024

(30) Foreign Application Priority Data
Aug. 23, 2021 (EP) ..................................... 21306136

(51) Int. Cl.
A61B 90/00 (2016.01)
A61B 34/20 (2016.01)
(52) U.S. Cl.
CPC ...... A61B 90/37 (2016.02); A61B 2034/2046 (2016.02); A61B 2034/2068 (2016.02)
(58) Field of Classification Search
None
See application file for complete search history.

(56) References Cited

U.S. PATENT DOCUMENTS

2002/0198451 A1 12/2002 Carson
2004/0106926 A1 6/2004 Leitner

OTHER PUBLICATIONS

Tsuji Masaki et al: "Joint line convergence angle predicts outliers of coronal alignment in navigated open-wedge high tibial osteotomy", Archives of Orthopaedic and Trauma Surgery, Springer Verlag, DE, vol. 140, No. 6, Aug. 30, 2019 (Aug. 30, 2019), pp. 704-715, XP037145485, ISSN: 0936-8051, DOI: 10.1007/S00402-019-03245-0, retrieved Aug. 30, 2019.
(Continued)

*Primary Examiner* — Andrew Yang
(74) *Attorney, Agent, or Firm* — Thomas | Horstemeyer, LLP

(57) ABSTRACT

The present disclosure relates to a system for guiding an osteotomy procedure on a tibia and/or a femur pertaining to a patient's lower limb to correct a misalignment of said lower limb, wherein a tibial tracker is fixed to the tibia and a femoral tracker is fixed to the femur, said system comprising a control unit configured to be coupled to a localization system adapted to track a position and orientation of the tibial tracker and the femoral tracker, wherein the control unit is configured to: —receive at least one target alignment parameter of the lower limb provided by a user; —determine a position of a set of characteristic points on the tibia and/or the femur relative to the tibial tracker and/or the femoral tracker; —track the positions of said characteristic points relative to the tibial tracker and/or the femoral tracker based on localization data of the set of characteristic points during application of mechanical constraints by the user onto the patient's knee, said tracked positions forming a knee measurement data set; —based on the knee measurement data set, adjust a function defining a model of the patient's knee; —based on at least one output of said function and on at least one alignment parameter of the lower limb in the constrained position, determine at least one correction param-
(Continued)

eter of the osteotomy procedure to be applied to the lower limb to achieve the target alignment parameter.

34 Claims, 9 Drawing Sheets

(56) References Cited

OTHER PUBLICATIONS

Kim Man Soo et al: "Intraoperative adjustment of alignment under valgus stress reduces outliers in patients undergoing medial opening-wedge high tibial osteotomy", Archives of Orthopaedic and Trauma Surgery, Springer Verlag, DE, vol. 137, No. 8, Jun. 7, 2017 (Jun. 7, 2017), pp. 1035-1045, XP036276882, ISSN: 0936-8051, DOI: 10.1007/S00402-017-2729-4 [retrieved on Jun. 7, 2017].

Jud, Lukas, et al., "The impact of limb loading and the measurement modality (2D versus 3D) on the measurement of the limb loading dependent lower extremity parameters", BMC Musculoskeletal Disorders, (2020) 21:418, https://doi.org/10.1186/s12891-020-03449-1.

Stulberg, et al., Columbus Primary Total Knee Replacement: A2- to 4- Year Follow-u of the Use of Intraoperative Navigation-derived Data to Predict Pre- and Postoperative Function, downloaded Mar. 13, 2024, https://www.healio.com/news/orthopedics/20120331/columbus-primary-total-knee-replacement-a-2-to-4-year-follow-up-of-the-use-of-intraoperative-na . . . (dated Oct. 1, 2008.

European Search Report in related European Application No. 21306136.9, mailed Feb. 4, 2022.

International Search Report in related PCT Application No. PCT/EP2022/073489, mailed Nov. 4, 2022.

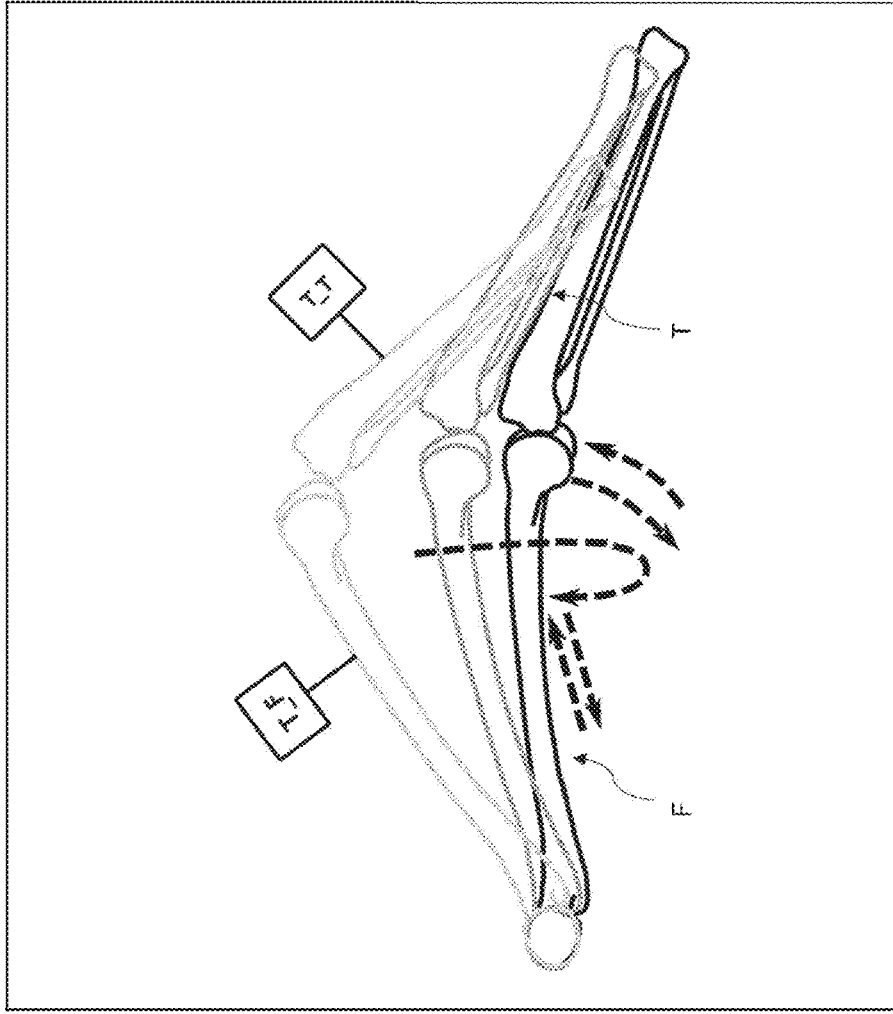
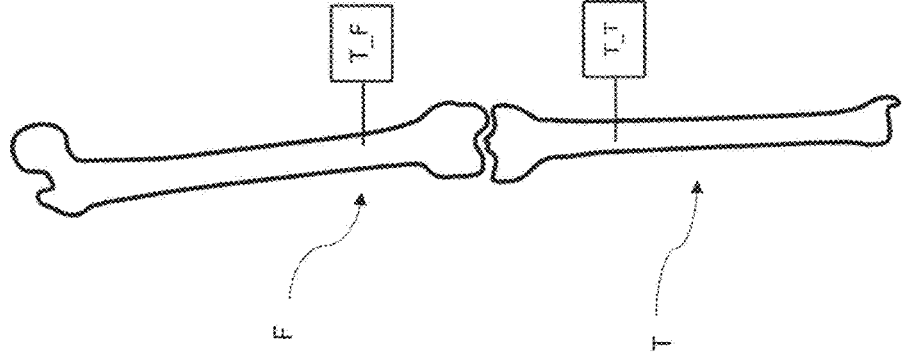
FIGURE 4

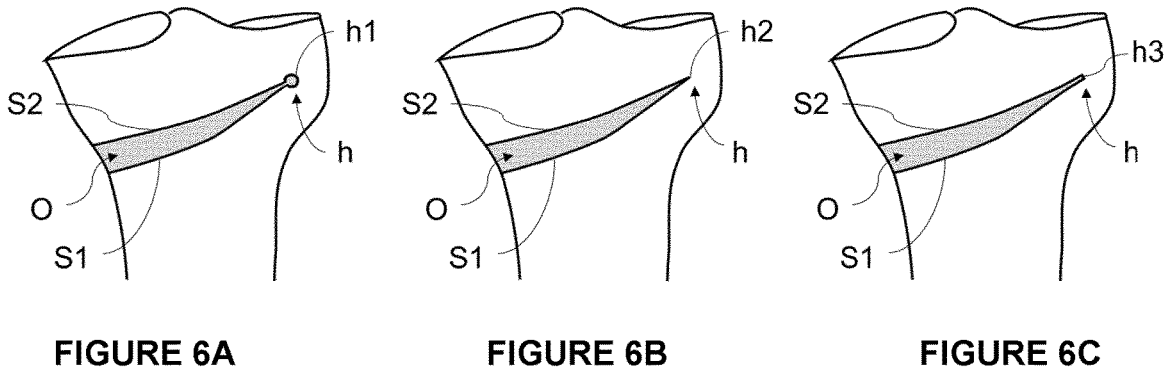
FIGURE 6A  FIGURE 6B  FIGURE 6C
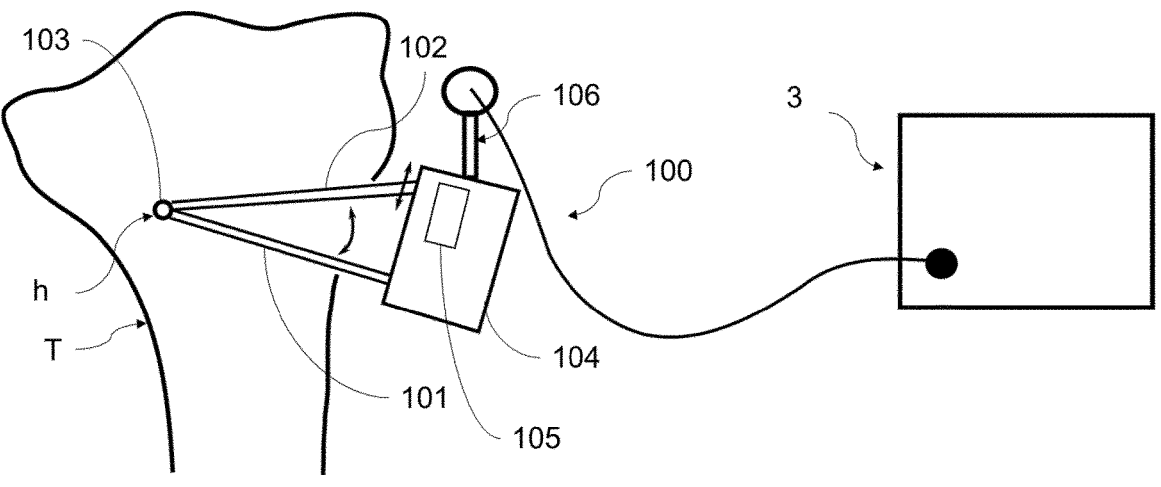
FIGURE 7

| 100 |
| :---: |
| 200 |
| 300 |
| 400 |
| 500 |
| 600 |
| 700 |

P
P1 = ... °/mm
P2 = ... °/mm
FIGURE 10A
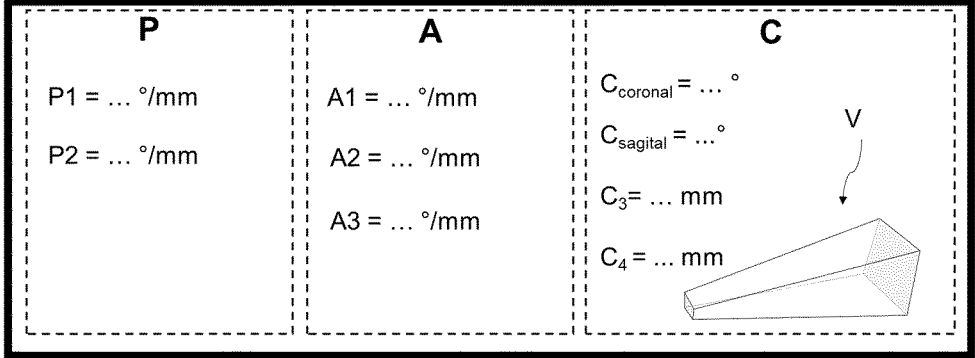
FIGURE 10B
| P | A |
|---|---|
| P1 = ... °/mm | A1 = ... °/mm |
| P2 = ... °/mm | A2 = ... °/mm |
| | A3 = ... °/mm |
P
P1 = ... °/mm
P2 = ... °/mm
A
A1 = ... °/mm
A2 = ... °/mm
A3 = ... °/mm
C
$C_{coronal} = ... °$
$C_{sagital} = ...°$
$C_3 = ... mm$
$C_4 = ... mm$
V
FIGURE 10C

SYSTEM FOR GUIDING AN OSTEOTOMY PROCEDURE

CROSS REFERENCE TO RELATED APPLICATIONS

This application is the 35 U.S.C. § 371 national stage application of PCT Application No. PCT/EP2022/073489, filed Aug. 23, 2022, which application claims the benefit of European Application No. EP 21306136.9 filed Aug. 23, 2021, both of which are hereby incorporated by reference herein in their entireties.

TECHNICAL FIELD

The present disclosure relates to a system for guiding an osteotomy procedure.

TECHNICAL BACKGROUND

Osteotomy is a surgical procedure used to correct a misalignment of a limb, in particular a lower limb (leg). To that end, an osteotomy procedure comprises cutting at least a portion of a bone of said limb to create a bone hinge and moving the bone ends around the hinge to achieve a better alignment of the limb. Once said alignment has been achieved, an implant is placed between the bone ends to maintain them in said position.

Osteotomy of a lower limb is complex and requires not only a precise diagnosis of the misalignment but also an accurate control of the surgical procedure itself.

Generally, the diagnosis of a misalignment is made based on a preoperative 2D X-ray image, in particular according to a frontal view, acquired in the standing position of the patient. The surgeon analyses said X-ray image and draws lines between characteristic points to determine alignment measurements. Based on said measurements, in particular the analysis of the hip-knee-ankle (HKA) alignment, a tibial and/or femoral cut is deduced, either open or closed. An open-wedge or closed-wedge osteotomy procedure is decided by the surgeon. This osteotomy cut will allow reorienting the bone in a three-dimensional space. The cut is generally wedge-shaped, with position and dimensions that can be determined from the 2D X-ray image.

During surgery, the patient lies down onto an operating table. Intraoperative X-ray images may be acquired to guide the surgical procedure. However, said intraoperative X-ray images are acquired in a different configuration of the patient's limb on the operating table, which in particular differs from the standing position due to the laxity of the joints and the influence of soft tissues surrounding the bones.

In order to properly diagnose the alignment problem, plan the osteotomy and achieve the corrected alignment, the surgeon must be able to assess the contribution of laxity and soft tissue to the correction of alignment and the differences between standing and lying positions, and also be able to control the surgical gesture throughout the course of the surgical plan.

Currently, navigation stations used for osteotomies around the knee offer laxity measurements, however, they do not offer automatic planning based on these measurements and a defined leg position. Indeed, the initial alignment measurements are performed with a sedated patient's leg simply placed on the operating table. These measurements therefore have uncertainties, of the order of several degrees according to the literature [Stulberg et al.] [Jud et al., 2020].

Once the surgical gesture for forming the opening or closing of the patient's bone has been achieved, and before fixing the implant to maintain the bone in the corrected position, the surgeon checks the alignment of the leg by placing a radiopaque cable along the patient's leg and acquiring an X-ray image allowing measuring the corrected alignment of the leg. If the expected correction has not been achieved, the surgeon carries out a new surgical gesture to improve the correction, and then checks again the achieved alignment with an X-ray image. The surgeon fixes the implant once he considers that a sufficient correction has be achieved. However, when the patient is in a standing position post-operatively, the laxity of the joints and the influence of the soft tissues generally modify the alignment of the leg, and may reveal an over- or an under-correction of the initial misalignment.

[Kim et al.] teach an open-wedge osteotomy procedure taking into account the laxity of the patient's leg. In this method, a preoperative X-ray image with the patient in standing position is acquired. Based on said X-ray image, the surgeon estimates an angle of opening and carries out the surgical gesture to obtain said angle. Then, the surgeon checks the alignment of the leg by placing a radiopaque cable along the patient's leg and acquiring an X-ray image allowing measuring the corrected alignment of the leg. During the acquisition of the X-ray image, the surgeon applies a valgus stress to the knee in order to simulate the effect of laxity and thus checks the alignment when the leg is in this constrained position. If the expected correction has not been achieved, the surgeon carries out a new surgical gesture to improve the correction, and then checks again the achieved alignment with an X-ray image, with the leg in the constrained position. The surgeon fixes the implant once he considers that a sufficient correction has been achieved. Since the corrected alignment is checked with the leg in constrained position, the risk of an over- or under-correction is reduced. However, this method may require a plurality of surgical gestures and intraoperative checks based on X-ray images to achieve a satisfactory alignment. As a result, the osteotomy procedure may be lengthy and expose the patient to a large dose of X-rays.

SUMMARY OF THE DISCLOSURE

The present disclosure relates to a system for guiding an osteotomy procedure that allows taking into account the laxity of the joints and the influence of soft tissues to determine and monitor a surgical plan.

To that end, the present disclosure presents a system for guiding an osteotomy procedure on a tibia and/or a femur pertaining to a patient's lower limb to correct a misalignment of said lower limb, wherein a tibial tracker is fixed to the tibia and a femoral tracker is fixed to the femur, said system comprising a control unit configured to be coupled to a localization system adapted to track a position and orientation of the tibial tracker and the femoral tracker, wherein the control unit is configured to:

receive at least one target alignment parameter of the lower limb provided by a user;

determine a position of a set of characteristic points on the tibia and/or the femur relative to the tibial tracker and/or the femoral tracker;

track the positions of said characteristic points relative to the tibial tracker and/or the femoral tracker based on localization data of the set of characteristic points during application of mechanical constraints by the user onto the patient's knee to simulate the effect of laxities and soft tissues onto the lower limb's alignment, said tracked positions forming a knee measurement data set;

based on the knee measurement data set, adjust a function defining a model of the patient's knee;

based on at least one output of said function and on at least one alignment parameter of the lower limb in the constrained position, determine at least one correction parameter of the osteotomy procedure to be applied to the lower limb to achieve the target alignment parameter.

By taking into account the laxity and influence of soft tissues for planning the surgical gesture, the correction parameter computed by the control unit is more accurate and more adapted to the patient's physiology. As a result, the risk of over- or under-correction of the misalignment is reduced, and the desired correction can be achieved directly, thereby reducing the number of iterations of surgical gestures and checks before fixing the osteotomy implant.

The knee measurement data set can comprise a set of ligament balance parameters, at least one laxity parameter and/or the at least one alignment parameter.

Advantageously, the function can be based on aggregation of patient data sets from intra-operative and post-operative alignment parameters of respective patients.

In some embodiments, the control unit is configured to modify the function based on machine learning methods to refine outputs of the function.

In some embodiments, the control unit is configured to monitor an evolution of the at least one alignment parameter based on localization data of the set of characteristic points during the osteotomy procedure.

The control unit can be further configured to determine, based on the at least one target alignment parameter and localization data of the set of characteristic points during the osteotomy procedure, whether each target alignment parameter is achieved.

The control unit can be further configured to monitor an evolution of a geometric feature of a volume being removed or created by the osteotomy cut relative to the at least one correction parameter.

In some embodiments, an additional tibial or femoral tracker is fixed to the bone so that two tibial or femoral trackers are fixed to the bone on both sides of the osteotomy cut, and the control unit is configured to compute the evolution of the osteotomy cut based on localization data of said two trackers.

In some embodiments, the system further comprises a mechanical device adapted to be inserted within the osteotomy cut and designed to expand or retract as the sides of the cut are moved farther or closer to each other, and at least one sensor coupled to the control unit and configured to measure in real time an expansion or a retraction of the mechanical device, and the control unit is configured to compute the evolution of the osteotomy cut based on measurement data from said at least one sensor.

In other embodiments, the system further comprises two mechanical devices adapted to be fixed to sides of the osteotomy cut, an adjustable link connecting said mechanical devices and designed to expand or retract as the sides of the cut are moved farther or closer to each other, and at least one sensor coupled to the control unit and configured to measure in real time an expansion or a retraction of the adjustable link, and the control unit is configured to compute the evolution of the osteotomy cut based on measurement data from said at least one sensor.

The system advantageously comprises a user interface coupled to the control unit, the user interface being configured to enter at least one user input, said user input comprising at least one of:

the at least one bone to be cut, an osteotomy type, such as an open-wedged osteotomy, a closed-wedge osteotomy or a more complex osteotomy, a number of cut to be made in each bone;

the at least one target alignment parameter.

The user interface may be configured to display each alignment parameter and/or correction parameter, and/or an indication that the at least one target alignment parameter is achieved.

The at least one target alignment parameter can comprise a mechanical femorotibial angle (mFTA), a mechanical medial proximal tibial angle (mMPTA), a mechanical lateral distal femoral angle (mLDFA), a lateral tibial plateau inclination (LTPI), a medial tibial plateau inclination (MTPI), a hip-knee-ankle angle (HKA), a joint line convergence angle (JLCA), a posterior tibial slope (PTS), a hip abduction angle (HAA), a tibial plafond inclination (TPI), a talar inclination angle (TIA), a lateral patellar tilt (LPT) and/or a lateral patellar shift (LPS).

The at least one correction parameter can comprise a geometric feature of a bone part to be removed from the tibia or femur and a geometric feature of a space created around the hinge to appear during distraction of the tibia or femur.

The control unit can be configured to determine the position of the set of characteristic points on the tibia and/or the femur relative to the tibial tracker and/or the femoral tracker based on at least one of the following methods:

segmenting at least one 2D and/or 3D medical image of the patient's limb and determining the set of reference characteristic points on said segmented image;

adjusting a bone model comprising the set of characteristic points to the patient's tibia or femur in at least one 2D and/or 3D image of the patient's limb using a bone morphing technique;

obtaining localization data of a pointer tracker fixed to a pointer palpating characteristic points on the tibia and/or the femur; and obtaining localization data of the femoral and tibial trackers as a user moves the limb about at least one joint.

In some embodiments, the control unit is configured to be coupled to an X-ray imaging system adapted to acquire 2D and/or 3D images of the lower limb of the patient.

In some embodiments, the knee measurement data set relates to one position of the patient's leg without any constraint applied to the knee and one position of the patient's leg with mechanical constraints applied to the knee.

In another aspect, the present disclosure relates to a method for guiding an osteotomy procedure on at least one bone selected from a tibia and a femur pertaining to a patient's lower limb to correct a misalignment of said lower limb, wherein a tibial tracker is fixed to the tibia and a femoral tracker is fixed to the femur. A localization system tracks a position and orientation of the tibial tracker and the femoral tracker. The method comprises:

receiving at least one target alignment parameter of the lower limb provided by a user;

determining a position of a set of characteristic points on the tibia and/or the femur relative to the tibial tracker and/or the femoral tracker;

applying mechanical constraints onto the patient's knee by a user to simulate effect of laxities and soft tissues onto the lower limb's alignment;

tracking positions of said characteristic points relative to at least one of the tibial tracker and the femoral tracker based on localization data of the set of characteristic points during application of said mechanical constraints, said tracked positions forming a knee measurement data set;

based on the knee measurement data set, adjusting a function defining a model of the patient's knee;

based on at least one output of said function and on the at least one alignment parameter of the lower limb in the constrained position, determining at least one correction parameter of the osteotomy procedure to be applied to the lower limb to achieve the target alignment parameter.

In some embodiments, the method further comprises carrying the osteotomy procedure, said osteotomy procedure comprising performing at least one osteotomy cut into the bone so as to form a hinge connecting two sides of the bone and moving said sides relative to each other around the hinge.

In some embodiments, the knee measurement data set comprises at least one of: a set of ligament balance parameters, at least one laxity parameter and at least one alignment parameter.

In some embodiments, the function is based on aggregation of patient data sets from intra-operative and post-operative alignment parameters of respective patients.

In some embodiments, the function can be modified over time based on machine learning methods to refine outputs of the function.

In some embodiments, the method comprises monitoring an evolution of the at least one alignment parameter based on localization data of the set of characteristic points during the osteotomy procedure.

In some embodiments, the method further comprises determining, based on localization data of the set of characteristic points during the osteotomy procedure, whether each target alignment parameter is achieved.

In some embodiments, the method further comprises monitoring an evolution of a geometric feature of a volume being removed or created by the osteotomy cut relative to the at least one correction parameter.

In some embodiments, the method further comprises:

fixing an additional tibial or femoral tracker to the bone so that two tibial or femoral trackers are fixed to the bone on both sides of the osteotomy cut; and computing an evolution of the osteotomy cut based on localization data of said two tibial or femoral trackers.

In other embodiments, the method further comprises:

inserting a mechanical device into the osteotomy cut and expanding or retracting said mechanical device as the user moves the sides of the cut farther or closer to each other; and measuring in real time an expansion or a retraction of the mechanical device by at least one sensor; and computing an evolution of the osteotomy cut based on measurement data from said at least one sensor.

In other embodiment, the method further comprises:

fixing two mechanical devices to both sides of the osteotomy cut, said mechanical devices being connected by an adjustable link;

expanding or retracting the adjustable link as a user moves the sides of the cut farther or closer to each other;

measuring in real time an expansion or a retraction of the adjustable link by at least one sensor; and computing an evolution of the osteotomy cut based on measurement data from said at least one sensor.

In some embodiments, the method comprises displaying, on a user interface, each alignment parameter and/or correction parameter, and/or an indication that the at least one target alignment parameter is achieved.

In some embodiments, the at least one target alignment parameter comprises at least one of: a mechanical femorotibial angle (mFTA), a mechanical medial proximal tibial angle (mMPTA), a mechanical lateral distal femoral angle (mLDFA), a lateral tibial plateau inclination (LTPI), a medial tibial plateau inclination (MTPI), a hip-knee-ankle angle (HKA), a joint line convergence angle (JLCA), a posterior tibial slope (PTS), a hip abduction angle (HAA), a tibial plafond inclination (TPI), a talar inclination angle (TIA), a lateral patellar tilt (LPT) and a lateral patellar shift (LPS).

In some embodiments, the at least one correction parameter comprises a geometric feature of a bone part to be removed from the bone and a geometric feature of a space created around the hinge to appear during distraction of the bone sides.

In some embodiments, the position of the set of characteristic points on the tibia and/or the femur relative to the tibial tracker and/or the femoral tracker is determined based on at least one of the following methods:

segmenting at least one 2D and/or 3D medical image of the patient's limb and determining the set of reference characteristic points on said segmented image;

adjusting a bone model comprising the set of characteristic points to the patient's tibia or femur in at least one 2D and/or 3D image of the patient's limb using a bone morphing technique;

obtaining localization data of a pointer tracker fixed to a pointer palpating characteristic points on the tibia and/or the femur; and obtaining localization data of the femoral and tibial trackers as a user moves the limb about at least one joint.

In some embodiments, the method comprises acquiring 2D images of the lower limb of the patient and determining the at least one target alignment parameter based on 2D X-ray images.

In some embodiments, the knee measurement data set relates to one position of the patient's leg without any constraint applied to the knee and one position of the patient's leg with mechanical constraints applied to the knee.

BRIEF DESCRIPTION OF THE FIGURES

Further features and advantages of the invention will appear in the following detailed description of embodiments, based on the appended drawings, in which:

FIG. 4 schematically illustrates the application of mechanical constraints to the knee in order to adjust a function defining a model of the patient's knee;

FIGS. 6A to 6C illustrate various geometric shapes of the space created around the hinge formed by an osteotomy cut;

FIG. 7 schematically illustrates a mechanical device allowing monitoring the retraction or distraction of the bone;

FIGS. 10A to 10E illustrate a screen of the user interface at successive stages of the osteotomy procedure.

Figure 1:
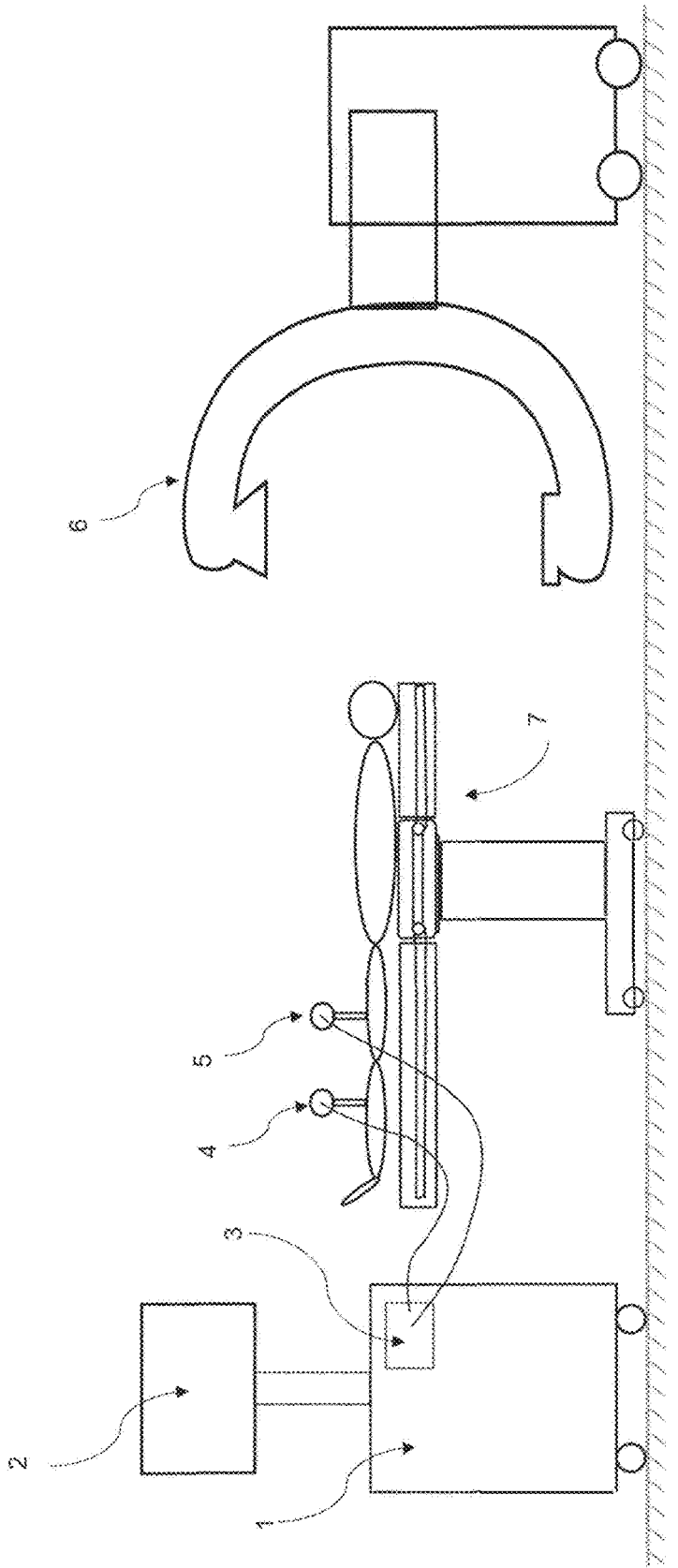
FIG. 1 illustrates a general overview of the surgical system.

For the sake of legibility of the figures, the drawings have been simplified and may not illustrate the whole patient's anatomy or all the structural details of the surgical system.

DETAILED DESCRIPTION OF EMBODIMENTS

The osteotomy procedure is planned and guided by a computer-assisted surgery system. In some embodiments, the system may be a navigation system.

The procedure can comprise a preoperative step in which the patient is in a standing position and an intra-operative step in which the patient is in a lying position.

The intra-operative step is not limited to the surgical gesture itself but also includes the determination of a surgical plan based on target alignment parameters.

The target alignment parameters can be defined in the preoperative step.

However, the preoperative step is optional; in particular such a preoperative step can be omitted if the surgeon uses data known in the art to determine a surgical plan. In such case, the target alignment parameters are defined in the intra-operative step.

General Overview of the Surgical System

The surgical system comprises a control unit which comprises at least one processor configured to implement algorithms, and a localization system, configured to track in real time the position and orientation of trackers fixed to the bones of the patient's limb.

Any localization technology may be used. In some embodiments, the localization system may include at least one camera and the trackers each comprise a respective set of markers with a unique geometry that can be detected by the camera. Said markers may be passive markers, such as disks or balls comprising a reflective surface adapted to reflect light from an infrared camera. Alternatively, the markers may be active markers that are themselves adapted to emit light, such as LEDs. In other embodiments, the localization system may include at least one electromagnetic emitter and receiver and the trackers may each comprise an electromagnetic receiver or emitter coupled to the localization system. In other embodiments, the localization may comprise accelerometers, gyroscopes and/or magnetometers, in particular IMU (Inertial Measurement Unit) sensors.

The control unit is coupled to the localization system so as to receive localization data regarding the trackers. The surgical system may also comprise a user interface allowing a user to interact with the control unit, in particular to enter data. The user interface can include at least one screen to display information computed by the control unit or/entered by the user.

The osteotomy procedure can also involve an X-ray imaging system, which may be in particular a C-arm. However, such an X-ray imaging system is optional.

In case an X-ray imaging system is used, the control unit is coupled to the X-ray imaging system so as to receive images acquired by the X-ray imaging system. Such a coupling allows placing in a common referential the 2D or 3D images, the trackers and the characteristic points seen on the 2D or 3D images and tracked by the surgical system.

FIG. 1 illustrates a general overview of a preferred embodiment of the surgical system.

In the operating room, the patient lies on an operating table 7. A tibial tracker 4 is fixed to the patient's tibia and a femoral tracker 5 is fixed to the patient's femur.

Next to the operating table 7, a navigation station 1 comprises a control unit 3 and a display 2 for the user interface. In some embodiments, the display may be tactile.

For example, the tibial and femoral trackers 4, 5 are electromagnetic trackers and belong to an electromagnetic localization system. The trackers are linked to the control unit 3 to provide the control unit with localization data. If additional electromagnetic trackers are used, as explained below, they are also linked to the control unit.

In some embodiments, the surgical system also comprises a 2D and/or 3D intra-operative X-ray imaging system 6 that can be brought next to the patient to acquire 2D and/or 3D images. For example, the X-ray imaging system is a C-arm.

The localization system and the X-ray imaging system are known per se and will not be described in detail in the present text. In particular, localization systems and X-ray imaging systems currently available on the market can be used for carrying out the osteotomy procedure.

The description will thus be focused on the configuration of the control unit that allows implementing the osteotomy procedure.

Osteotomy Procedure

An osteotomy procedure consists in realizing a tibial and/or a femoral osteotomy with the aim to correct a misalignment of a limb (the limb comprising a tibia and a femur).

Figure 2A:
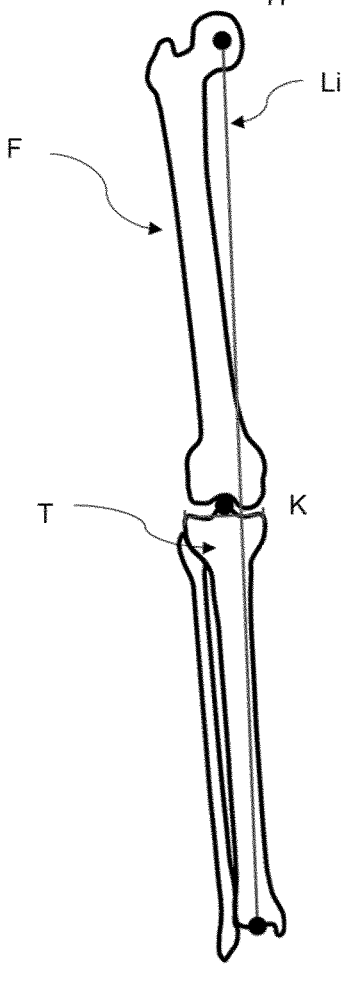
FIG. 2A schematically illustrates a varus alignment of a patient's leg before an open-wedge high tibial osteotomy.
Figure 2B:
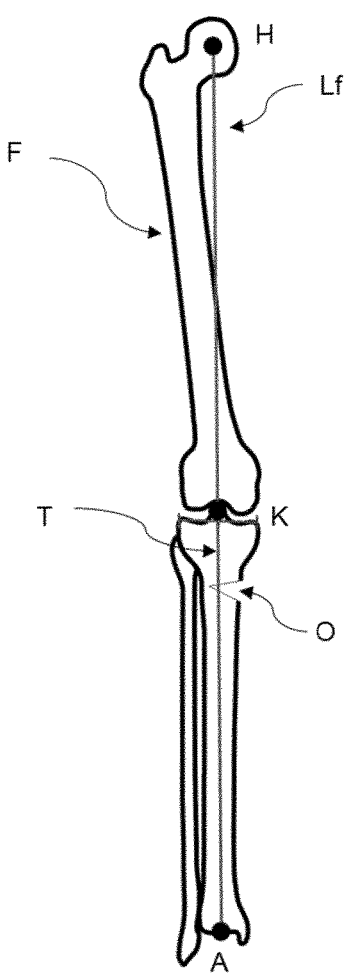
FIG. 2B schematically illustrates the leg alignment after an open-wedge high tibial osteotomy.

FIGS. 2A and 2B schematically illustrate the principle of an open-wedge high tibial osteotomy on a patient's right leg including a tibia T and a femur F seen according to a frontal view.

The knee joint has a knee center K. There are commonly multiple definitions of the knee center. The knee center can be defined, for instance, as the center of the apex of the femoral notch, the midpoint of the femoral condyles, the center of tibial spines, the midpoint of soft tissue outline or the midpoint of tibial plateaus. The femur F has a proximal joint, the hip joint and a center located in the hip ball (hereafter hip center H) which makes the interface with the pelvis (not shown). The tibia T has a distal joint, the ankle joint and a center (here after ankle center A) which makes the interface with the foot (not shown). As for the knee center, there are commonly multiple definitions of the ankle center. The ankle center can be defined, for instance, as the center of soft tissue near both the malleoli, the center bones near both the malleoli or the center of talus.

The present application is applicable to each of the above definitions.

In FIG. 2A, before osteotomy, one can observe a varus alignment of the leg. Indeed, the initial weight-bearing line Li (also called Mikulicz line) which passes through the hip and ankle centers H, A is located inwardly with respect to the knee center K. To correct this misalignment, an open-wedge osteotomy has been carried out to cut the higher part of the tibia to form a hinge and space apart the two parts of the tibia about said hinge. The space created by the distraction is designated by O in FIG. 2B. One can observe that, after osteotomy, the final weight-bearing line Lf passes through the hip, knee and ankle centers H, K and A. Of course, other types of osteotomies exist and the skilled person knows what type of osteotomy should be used for a given type of misalignment.

The osteotomy procedure requires the determination of target alignment parameters. Said target alignment parameters may be determined in a preoperative step or in the intra-operative step.

Determination of the Target Alignment Parameter(s)

Various target alignment parameters may be used and may be selected by the surgeon depending on the specific condition of the patient.

For example, but not limitatively, the target alignment parameter may be:

a mechanical femorotibial angle (mFTA), a mechanical medial proximal tibial angle (mMPTA), a mechanical lateral distal femoral angle (mLDFA), a lateral tibial plateau inclination (LTPI), a medial tibial plateau inclination (MTPI), a hip-knee-ankle angle (HKA): angle between the mechanical axes of the femur and the tibia, a joint line convergence angle (JLCA): angle made by a tangential line between the femoral condyles and the tibial plateau, a posterior tibial slope (PTS), a hip abduction angle (HAA), a tibial plafond inclination (TPI), a talar inclination angle (TIA), a lateral patellar tilt (LPT), and/or a lateral patellar shift (LPS).

The target alignment parameter(s) may be determined by various techniques.

In some embodiments, the target alignment parameters can be determined based on 2D X-ray images, by measurements of specific features representative of the alignment of the leg.

Said 2D X-ray images can be acquired pre-operatively. In such case, the patient is generally in standing position. The pre-operative step can thus allow diagnosing directly a misalignment of the patient's leg and consequently determining the target alignment parameter(s) to be achieved by the osteotomy procedure to provide a correct alignment of the leg.

Alternatively, said 2D X-ray images can be acquired intra-operatively. In such case, the patient is generally lying on the operating table. In order to take into account laxities and influence of soft tissues, the surgeon applies mechanical constraints to the leg in order to achieve an alignment similar to the alignment that would be observed in the standing position. The surgeon uses his/her professional expertise and knowledge of patients' anatomy to apply suitable mechanical constraints and thus simulate the alignment in the standing position. As mentioned for the pre-operative step, the surgeon can then determine the target alignment parameter(s) to be achieved by the osteotomy procedure to provide a correct alignment of the leg.

Due to the length of the leg, it may not be possible or suitable to obtain a single X-ray image of the whole leg. Thus, several images of different parts of the leg can be acquired and recorded to allow determining target alignments of the leg.

However, the use of X-ray images is not compulsory to determine the target alignment parameters in the intra-operative step. For example, thanks to the localization system, the surgical system alone can be sufficient to determine the relative positions of the femur and the tibia in all directions of a three-dimensional space, diagnose a misalignment of the leg and determine the target alignment parameter(s) to be achieved by the osteotomy procedure to provide a correct alignment of the leg. This allows reducing the patient's exposure to X-rays.

The target alignment parameter(s) is (are) used as an input for planning the surgical gesture in the intra-operative step.

Preparation of Intra-Operative Step

In the intra-operative step, the patient is placed lying down on an operating table of a surgical room and sedated.

At least two trackers are fixed to the lower limb: at least one tracker is fixed to the tibia and at least one tracker is fixed to the femur. By "fixed" is meant a temporary (the tracker being intended to be removed after the surgical procedure) but rigid fixation of the tracker to the respective bone, so as to avoid any movement of the tracker relative to the bone during the surgical procedure. For example, each tracker may be implanted into the respective bone using a pin or a screw. A coordinate system is attached to each tracker and is thus tracked in real time by the localization system.

In addition, one additional tracker may be fixed to the bone to be cut, so that one tracker is fixed to a respective side of the osteotomy cut. Thanks to the additional tracker, the control unit can follow in real time the degree of opening or closing of the wedge formed by the osteotomy. However, as mentioned below, other devices can be used to follow the advancement of the osteotomy, and the use of such an additional tracker is thus optional.

Figure 3:
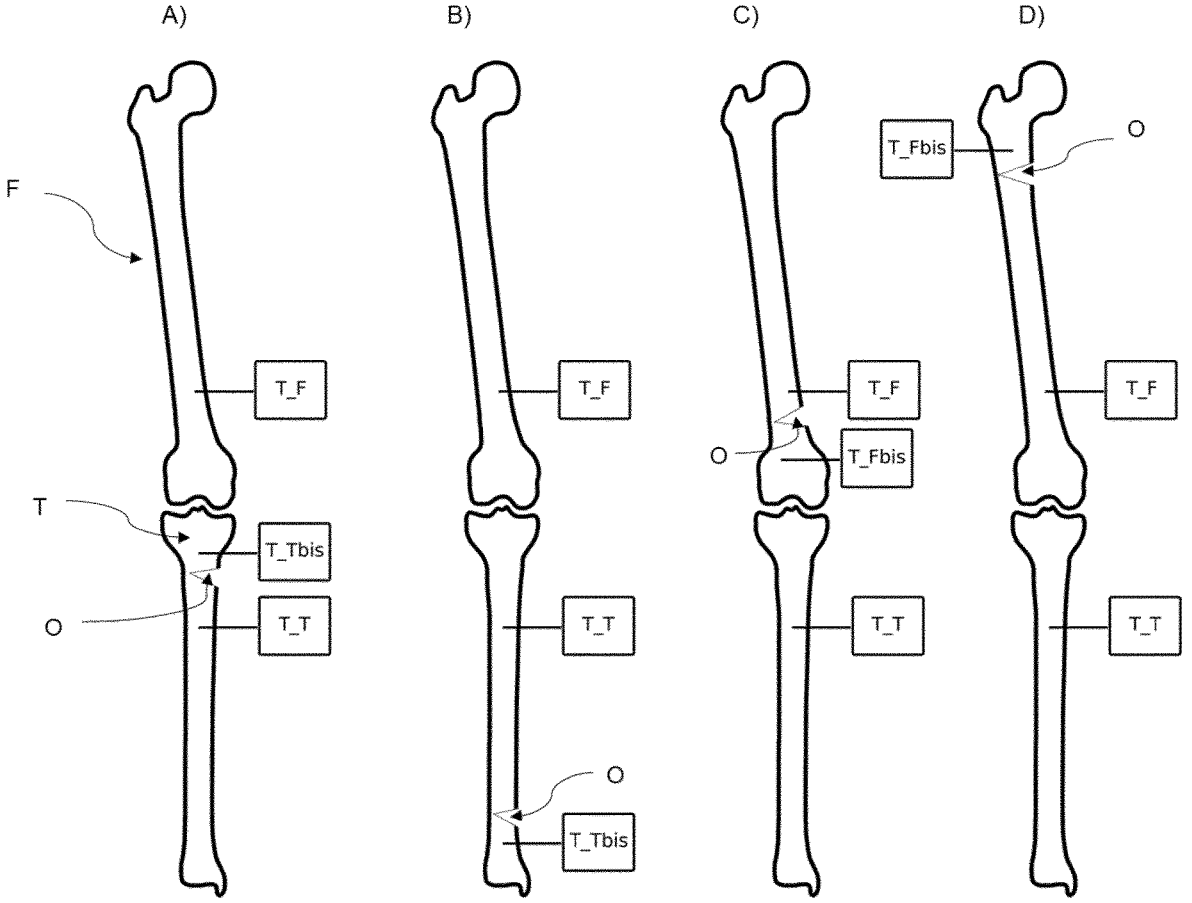
FIG. 3 schematically illustrates various embodiments of trackers placement for an osteotomy procedure.

FIG. 3 illustrates various embodiments of trackers placement.

In embodiment a), which corresponds to high tibial osteotomy, one tracker T_F is fixed to the femur F and two trackers T_T and T_Tbis are fixed to the tibia. The tracker T_Tbis is fixed to the upper part of the tibia, above the space O opened by osteotomy, and the tracker T_T is fixed to the lower part of the tibia, below the space O.

In embodiment b), which corresponds to distal tibial osteotomy, one tracker T_F is fixed to the femur F and two trackers T_T and T_Tbis are fixed to the tibia. The tracker T_Tbis is fixed to the lower part of the tibia, below the space O opened by osteotomy, and the tracker T_T is fixed to the upper part of the tibia, above the space O.

In embodiment c), which corresponds to distal femoral osteotomy, one tracker T_T is fixed to the tibia T and two trackers T_F and T_Fbis are fixed to the femur. The tracker T_Fbis is fixed to the lower part of the femur, below the space O opened by osteotomy, and the tracker T_F is fixed to the upper part of the femur, above the space O.

In embodiment d), which corresponds to high femoral osteotomy, one tracker T_T is fixed to the tibia T and two trackers T_F and T_Fbis are fixed to the femur. The tracker T_Fbis is fixed to the upper part of the femur, above the space O opened by osteotomy, and the tracker T_F is fixed to the lower part of the femur, below the space O.

These embodiments can be combined if appropriate, for example if an osteotomy cut has to be made on both the femur and the tibia (double level osteotomy).

The trackers T_Tbis and T_Fbis can be omitted if another device is used to track the advancement of the osteotomy procedure.

Determination of Characteristic Points

A set of characteristic points on the tibia and/or the femur is defined, with the position of said characteristic points in the coordinate system of at least one tracker being known.

Various methods for determining said set of characteristic points may be used.

In some embodiments, the characteristic points may be acquired by palpation using a pointer carrying a tracker tracked by the localization system. In such a way, the position of each palpated point relative to at least one of the tibial and femoral trackers can be determined.

In other embodiments, the characteristic points may be determined on at least one 2D (bi-dimensional) or 3D (three-dimensional) X-ray image whose position in the coordinate system of at least one tracker is known. Preferably, said 2D or 3D X-ray image is acquired in the intra-operative step. Alternatively, the 2D or 3D X-ray image can be acquired pre-operatively. In such case, the control unit computes a registration between the pre-operative 2D or 3D X-ray image and the coordinate system of at least one of the tibial and femoral trackers.

The characteristic points can be identified based on a segmentation of the 2D or 3D X-ray image(s). For instance, the knee joint center can be located in at least one 2D or 3D image of the knee, via the analysis of one or more characteristic point(s) found on the images. In particular, different characteristic points of the image can be used to define the knee center. For instance, the knee center can be the average of two or more points: the midpoint of the femoral condyles or the center of the soft tissue outline.

Otherwise, the characteristic points may be present on a model of the bone and said model may be adjusted to the patient's bone using known bone morphing techniques, so as to register the characteristic points with a 2D or 3D X-ray image of the patient's bone.

Some characteristic points (for example, the center of a joint) may also be determined by moving the limb or a part of the limb about a joint. For example, the knee joint center can be located by using a morpho-functional method using flexion-extension movements. In such a morpho-functional method, 3D positions and orientations of the femoral and tibial trackers are recorded during the motion by the surgical system. An average rotation axis representing the flexion/extension is estimated.

Said methods are known by the skilled person and will not be described in detail in the present case.

Of course, the above methods can be combined to determine the characteristic points. For example, the hip, knee or ankle center can be obtained via the morpho-functional method and be adjusted via the information of the position of other characteristic points on a 2D or 3D X-ray image. In other situations, a partial determination of the characteristic points based on an incomplete segmentation or an incomplete bone morphing can be supplemented by the palpation of other characteristic points with a tracked pointer.

Adjustment of a Function Defining the Patient's Knee

Initially, the leg is in a free position, i.e. it lies on the operating table without any constraint. As mentioned in the introduction, the alignment of the bones is different from the standing position, due to the laxity of the joints and the influence of the soft tissues surrounding the bones.

Then, the surgeon manipulates the leg to apply mechanical constraints to the knee so as to bring the lower limb in a one or a plurality of constrained positions. The direction and amplitude of said mechanical constraints are selected by the surgeon based on his clinical expertise, in view of simulating the effect of laxities and soft tissues on the lower limb's alignment. Said mechanical constraints may be defined by known clinical tests. Such clinical tests include, but are not limited to: the valgus stress test—or medial stress test, in which the surgeon holds the patient's femur and pushes or pulls the tibia; and the Lachman test, in which the patient's knee is flexed to about 20°, the surgeon holds the distal part of the femur with one hand and exerts an anterior traction of the tibia with the other hand.

Since the position of the characteristic points is known in the coordinate system of at least one of the trackers, it is possible to track the position of said characteristic points over time when the surgeon manipulates the leg.

In particular, the position of the characteristic points in each constrained position of the leg is determined and recorded by the control unit.

Thus, a knee measurement data set is determined and recorded by the control unit. Preferably, said data set is computed in all directions in order to take into account more accurately the patient's condition.

The knee measurement data set can comprise a set of ligament balance parameters, at least one laxity parameter and/or at least one alignment parameter.

FIG. 4 schematically illustrates the application of the mechanical constraints and the computation of a correction in the frontal plane, for an open-wedge high tibial osteotomy.

From the left to the right of the figure:

the leg is in the free position, at least one tibial and femoral tracker T_T, T_F being fixed to the tibia and the femur, respectively;

the surgeon applies mechanical constraints to the leg represented by the arrows in order to simulate the effect of laxities and soft tissues: the positions of the leg in the constrained position are illustrated in dotted lines, superimposed with the free position (solid line); at each of said constrained positions, the position of the characteristic points is determined and recorded by the control unit.

In some embodiments, each constrained position can be indicated by the control unit to the surgeon, or, conversely, the surgeon can indicate to the control unit at which position the leg is constrained. At each constrained position the characteristic points are determined and recorded by the control unit. Switching from one constrained position to the next one can be realized by pressing a button or a pedal.

In other embodiment, one simple case would be that at the final constrained position, the position of the characteristic points is determined and recorded by the control unit. Said final constrained position can be indicated by the surgeon to the control unit for example by pressing a button or a pedal when he/she considers that said constrained position is representative of the effect of laxities and soft tissues.

In other embodiments, the surgeon may be given a determined time to manipulate the leg (for example, 30 seconds) and during this time the positions of the characteristic points are determined and recorded by the control unit. At the end of said determined time, the control unit may take into account the data acquired and checks whether it constitutes a sufficient input to define a model of the patient's knee.

For all previous embodiments, the application of the mechanical constraints can be done at least partially by a robotic arm or any other suitable mechanical device controlled by the control unit.

Based on said knee measurement data set, the control unit is configured to either take one constraint position and the localization of the characteristic points at that position to initialize the planning of the osteotomy or to adjust a complex function that defines a model of the patient's knee for planning the osteotomy.

The complex function establishes a relationship between each alignment parameter in a constrained position and said alignment parameter in the free position. Indeed, the alignment parameters may vary depending on the constraints applied to the leg by the ligaments and soft tissues.

Said complex function thus aims at predicting the optimal correction for reaching a post-operative alignment. For instance, the patient's degree of laxity for each knee ligament can be assessed from the patient knee model obtained from the measurement data set. It is of importance to be able to determine patient's inherent laxity prior to the osteotomy since the degree of correction and the final alignment can be affected by the inherent laxity and can lead to over or under-correction if not taken into account. For example, for two different patients having a same alignment parameter in the free position, the post-operative alignment may be different depending on the laxity of his/her knee ligaments.

The function receives as inputs in particular measurements of characteristic points of the patient's leg, the type of osteotomy (open-wedged, closed-wedged, or complex), the number of cuts, and issues as outputs correction parameters adapted to correct a misalignment of the leg.

The complex function has been generated before the implementation of the osteotomy procedure. It can be based on aggregation of patient data sets from intra-operative (input) and post-operative (result) alignment parameters of respective patients.

Advantageously, based on machine learning methods, the control unit can modify and adjust the complex function to refine its outputs.

To that end, after the osteotomy procedure is finished, and just before removing tibial and femoral trackers, another measurement data set may be acquired with the surgeon applying mechanical constraints on the leg. For each patient, the knee model associated with the knee measurement dataset measured after the osteotomy procedure is compared to the initial measurement data. With this comparison the complex function that helps determining at least one correction parameter of the osteotomy procedure can be tuned and is thus improved to fit better the complex cross interactions of laxities and bone alignments for the next patients. Such machine learning algorithms are known per se and will thus not be described in detail in the present text. Such algorithms may involve neural networks that can be trained by processing data sets including, as inputs, the initial alignment parameter(s) of the patient and the applied correction parameter(s) and, as results, the final alignment parameter(s).

In some embodiments, the control unit can use a simpler function. To that end, the knee measurement data set is limited to two intra-operative positions of the patient's leg:
the free position, and
a constrained position in which mechanical constraints are applied to the leg.

In such case, the constrained position is chosen to be sufficiently relevant in view of the patient's pathology. For example, if the patient suffers from a varus to be corrected by an open-wedge tibial osteotomy, the constrained position must be a valgus position to allow the function to provide a suitable correction.

Alignment parameters are determined for each of said two positions and the control unit determines a function that establishes a relationship between an alignment parameter in the constrained position and the corresponding alignment parameter in the free position. Said function can comprise or combine translations or rotations and can be determined based on respective positions of the characteristic points in both positions.

Figure 5:
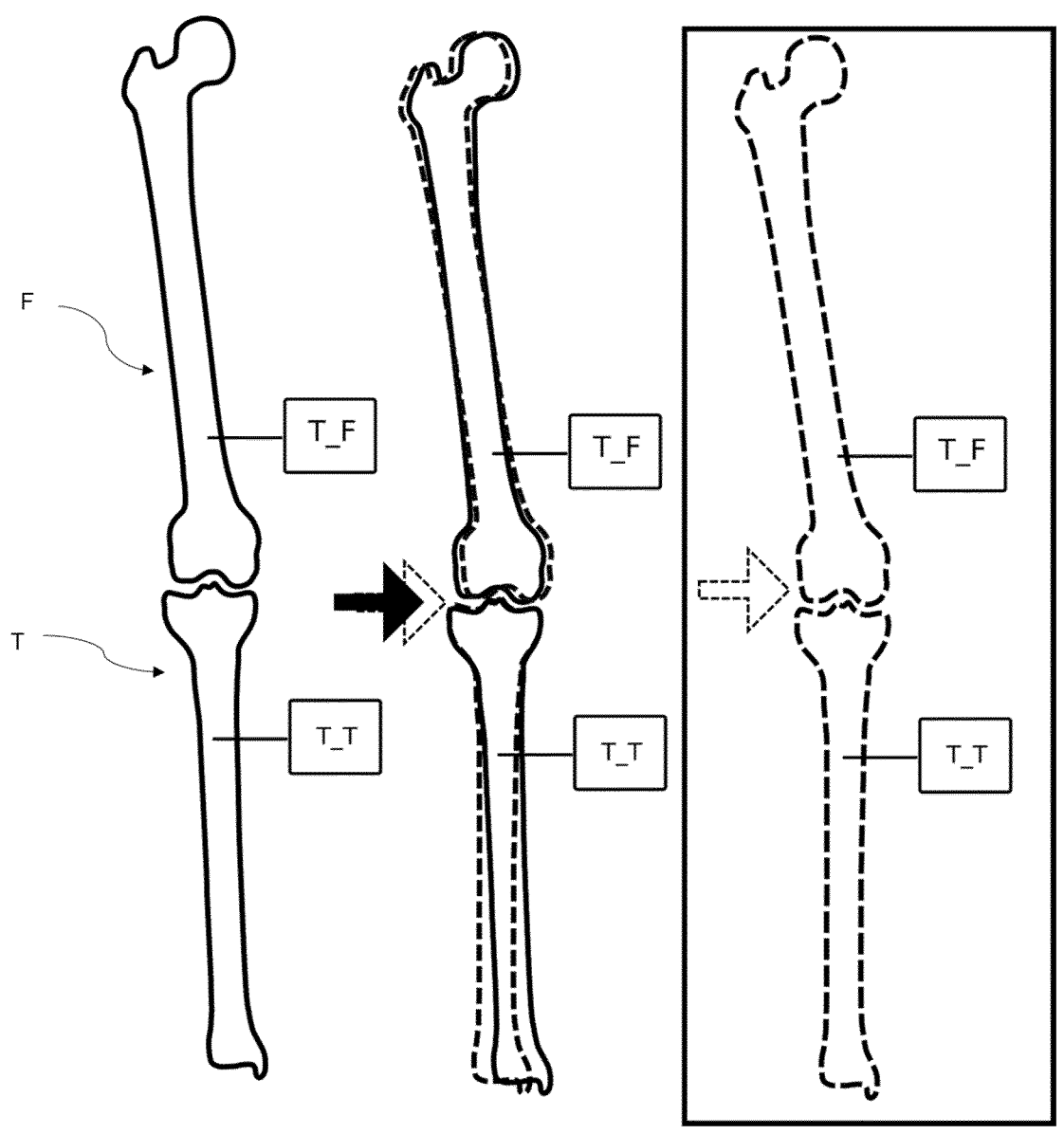
FIG. 5 schematically illustrates the measurement of the alignment parameters with the leg in one constrained position.

FIG. 5 schematically illustrates the application of such mechanical constraints to achieve a single constrained position and the computation of a correction in the frontal plane, for an open-wedge high tibial osteotomy.

From the left to the right of the figure:
the leg is in the free position, at least one tibial and femoral tracker T_T, T_F being fixed to the tibia and the femur, respectively;
the surgeon applies mechanical constraints to the leg in order to simulate the effect of laxities and soft tissues: the position of the leg in the constrained position is illustrated in dotted lines, superimposed with the free position (solid line);
at the final constrained position, the position of the characteristic points is determined and recorded by the control unit. Said final constrained position can be indicated by the surgeon to the control unit for example by pressing a button or a pedal when he/she considers that said constrained position is representation of the effect of laxities and soft tissues.

Computation of Surgical Plan

Then, the surgical plan can be automatically computed by the control unit.

To that end, the control unit receives the target alignment parameter(s) input by the surgeon. For example, said target alignment parameters may be entered by the surgeon through a user interface coupled to the control unit. The target alignment parameter(s) can be determined by the surgeon as explained above, based on measurements on 2D or 3D X-ray images, or based on data provided by the surgical system. Alternatively, the target alignment parameter(s) can be set arbitrarily by the surgeon, based on his/her own experience and the clinical state of the art.

The surgeon can also decide the bone(s) to be cut and the number of cuts to be performed to achieve the desired correction. Indeed, for open-wedge osteotomy, the bone can typically be cut according to one or two planes (formed by one or two cuts, respectively). For closed-wedge osteotomy, the bone can typically be cut according to one or two planes (formed by two or three planes, respectively. However, the surgeon may choose to carry out a more complex osteotomy, requiring additional planes and cuts.

The surgeon can then input the type of osteotomy he intends to implement (open-wedge, closed-wedge or more complex) and the number of cutting planes (one plane, two planes or more complex). For a complex osteotomy, the surgeon can indicate on a model displayed by the user interface the location and geometry of the planes and cuts.

Based on the input type of osteotomy and number of bone cuts, on the target alignment parameter(s) and on the output(s) of the function defining a model of the patient's knee, the control unit computes at least one correction parameter. Such a correction parameter generally corresponds to an amount of bone distraction or removal to achieve in order to obtain the desired alignment of the limb. More precisely, for each bone cut, the planning provides the geometry and the correction angle to be achieved:
geometry and angle of the bone part to be removed by the osteotomy cut(s), in the case of a closed-wedge osteotomy;
geometry and angle of the space created around the hinge that will appear during distraction in the case of an open-wedge osteotomy.

FIGS. 6A-6C illustrate various shapes of the hinge h that can be obtained after cutting the bone and distracting the two sides S1, S2 of the bone to create the space O. In the embodiment of FIG. 6A, after cutting the bone with a saw, an additional drilling is made at the junction between the two sides S1, S2 in order to form a tunnel h1 having a circular cross section. In the embodiment of FIG. 6B, the hinge is in the form of a line h2 obtained at the junction of the two sides S1, S2 cut by the saw. In the embodiment of FIG. 6C, after cutting the bone with the saw, an additional milling is made at the junction between the two sides S1, S2 in order to form a flat end surface h3. Additional shapes such as h1 and h3 may allow reducing the risk of breaking the bone remaining around the hinge. Of course, the skilled person may choose any other shape if more appropriate.

If the correction requires several bone cuts, the planning provides the geometry and correction angle for each bone cut.

The final alignment parameters that should be obtained after the surgical procedure that would take into account the contribution of laxity and soft tissues can be predicted by applying the computed correction parameter(s) to the alignment parameter(s) measured in the initial (free) position.

The surgeon can validate the surgical plan or modify it based on his/her professional skills and experience. The modification of the surgical plan may be made through the user interface mentioned above.

In case the simpler function described above is used, the function is used to determine target alignment parameters in the free position based on the target alignment parameters input by the surgeon. The correction parameter(s) can thus be determined as a difference between a target alignment parameter in the free position and the measured alignment parameter in said free position.

Implementation of Surgical Gesture

Once the surgical plan has been finalized, the surgeon can carry out the surgical gesture in accordance with the surgical plan. To that end, he/she may be assisted by a robot, by the surgical system, and/or by intra-operative X-ray imaging. During the surgery, the mechanical constraints (e.g. valgus stress) may be maintained or released.

In any case, the surgeon may monitor in real time the progress of the surgical intervention, for example thanks to a screen coupled to the control unit and displaying the evolution of the current correction relative to the correction parameter for each bone cut.

In some embodiments, said evolution can be monitored using two trackers fixed to the bone being cut, on both sides of the cut. To that end, an additional femoral or tibial tracker is fixed to the bone, on the other side of the cut with respect to the previously mentioned femoral or tibial tracker (see examples in FIG. 3). Based on localization data of said trackers, the control unit can determine in real time the relative position of both parts of the bone being cut.

In other embodiments, a mechanical device may be inserted within the cut, and be designed to expand or retract as the parts of the bone being cut are moved farther or closer to each other. Said mechanical device may include at least one sensor coupled to the control unit and configured to measure in real time an expansion or a retraction of the mechanical device.

FIG. 7 schematically illustrates an embodiment of such a medical device.

The mechanical device 100 comprises two plates 101, 102 connected to a mechanical hinge 103. The plates 101, 102 are coupled to a body 104. The plates are pivotable relative to each other about the mechanical hinge 103.

The angle between the two plates 101, 102 is precisely measured with an angle sensor 105 arranged in the body 104. The measurement data from the sensor 105 is sent to the control unit 3.

The mechanical device 100 further includes a tracker 106 belonging to the same localization system as the tibial and femoral trackers (that are not represented in FIG. 6 for sake of legibility of the figure). For example, the tracker 106 is an electromagnetic tracker and is linked to the control unit 3 in order to provide to the control unit localization data regarding the mechanical device 100 during its operation.

In case of closed-wedge osteotomy, the plates 101, 102 are inserted into the resected bone wedge so that the mechanical hinge 103 coincides with the bone hinge h, in order to monitor how the bone is retracted. Indeed, closing the wedge about the hinge h causes the plates 101, 102 to be moved toward each other, thereby decreasing the angle between the plates 101, 102, which is measured by the sensor 105.

In case of open-wedge osteotomy, the plates 101, 102 are inserted into the slot of the osteotomy bone cut, so that the mechanical hinge 103 coincides with the bone hinge h, in order to monitor how the bone is distracted. Indeed, distracting the bone parts about the hinge h causes the plates 101, 102 to be moved away from each other, thereby increasing the angle between the plates 101, 102, which is measured by the sensor 105.

Although illustrated in the tibia T in FIG. 6, the mechanical device 100 may be used in a similar way in case of femoral osteotomy.

In other embodiments, two mechanical devices may be fixed to both parts of the bone being cut, and linked by an adjustable link that is designed to expand or retract as the parts of the bone being cut are moved farther or closer to each other. Said link may include at least one sensor coupled to the control unit and configured to measure in real time an expansion or a retraction of the link.

Figures 8, 9:
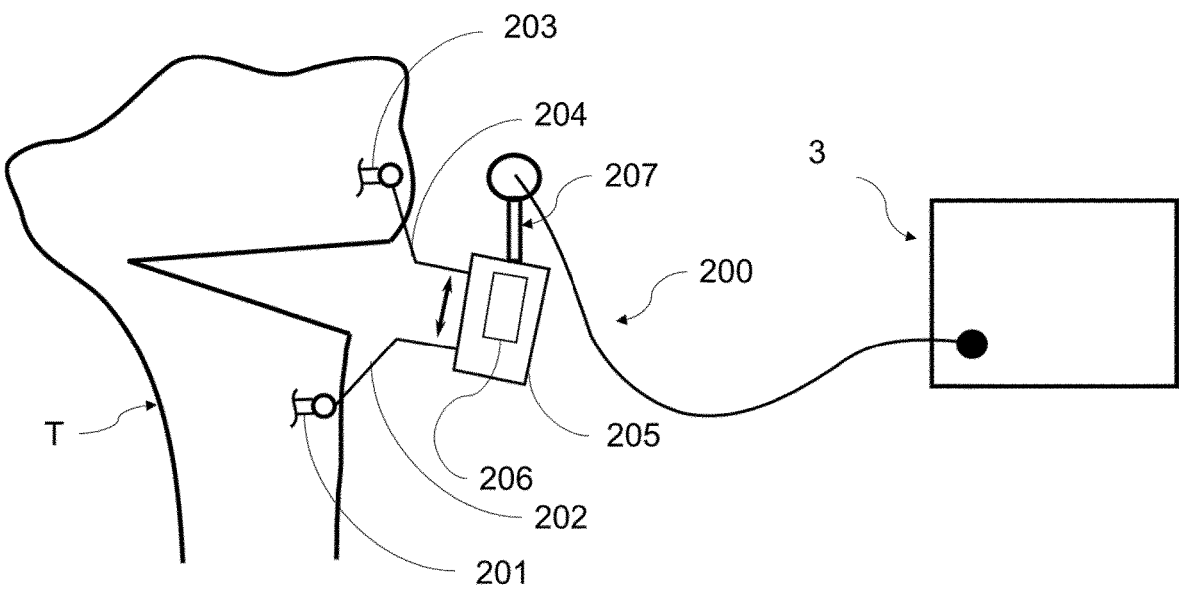
FIG. 8 schematically illustrates a mechanical assembly allowing monitoring the retraction or distraction of the bone.
FIG. 9 is a flowchart of the osteotomy procedure carried out with the surgical system.

FIG. 8 schematically illustrates an embodiment of such mechanical devices.

The mechanical assembly 200 comprises a body 205 and two plates 202, 204 connected to the body 205 by a hinge inside the main body.

Each plate 202, 204 is rigidly fixed to a respective part of the bone (e.g. the tibia T) around the osteotomy cut by a pin 201, 203 implanted into the bone.

The plates are movable relative to each other, thereby allowing moving the parts of the bone (and thus the pins 201, 203) closer or farther to each other about the hinge h.

The distance between the two pins 201, 203 is precisely measured with a displacement sensor 206 arranged in the body 205. The measurement data from the sensor 105 is sent to the control unit 3.

The mechanical assembly 200 further includes a tracker 207 belonging to the same localization system as the tibial and femoral trackers (that are not represented in FIG. 7 for sake of legibility of the figure). For example, the tracker 207 is an electromagnetic tracker and is linked to the control unit 3 in order to provide to the control unit localization data regarding the mechanical assembly 200 during its operation.

In case of closed-wedge osteotomy, the mechanical assembly is fixed below and above the resected bone wedge, so as to monitor how the bone is retracted.

In case of open-wedge osteotomy, the mechanical assembly is fixed below and above the slot of the osteotomy bone cut, so as to monitor how the bone is distracted.

The mechanical devices may be used in a similar way in case of femoral osteotomy.

Verification of the Alignment Parameter(s)

The planned correction is monitored until the end of the surgical procedure. Before fixing the implant, a difference between the planned correction and the correction actually performed by the surgeon can be displayed.

If said difference is considered by the surgeon to be clinically acceptable, the surgeon can then proceed with the final positioning and fixation of the osteotomy implant.

If said difference is considered by the surgeon to be not clinically acceptable, the surgeon can then proceed to further bone distraction or removal, until the difference between the planned correction and the actual correction is considered to be acceptable.

When the planned bone distraction or removal has been achieved, but before fixing the osteotomy implant, the surgeon may also check the final alignment parameter(s). Hence, optionally, the surgeon applies the same mechanical constraints as previously and measures, thanks to the surgical system and/or X-ray imaging system, the alignment parameter(s), preferably in all directions. The control unit then computes differences between the achieved alignment parameters and the target alignment parameters.

If said differences are considered by the surgeon to be clinically acceptable, the surgeon can then proceed with the final positioning and fixation of the osteotomy implant.

If said differences are considered by the surgeon to be not clinically acceptable, the surgeon can then proceed to further bone distraction or removal, until the final alignment parameter(s) achieve(s) the desired target.

Summary of the Osteotomy Procedure

The osteotomy procedure is summarized in the flow chart of FIG. 9.

In step 100, input parameters are entered by the surgeon into the surgical system via the user interface to be used as input for the intra-operative step.

As mentioned above, the input parameters can include in particular:

the bone(s) to be cut (tibial osteotomy, femoral osteotomy, or double level osteotomy), the type of osteotomy (open-wedged, closed-wedge or more complex), the number of cuts, one or more target alignment parameter(s).

In step 200, characteristic points of the tibia and/or the femur are defined and localized such that the position of said characteristic points in the coordinate system of at least one tracker is known.

In step 300, the surgeon manipulates the leg to apply mechanical constraints to the knee. The position of the characteristic points in each constrained position of the leg is determined and recorded by the control unit. Said knee measurement data set is used by the control unit to adjust the complex function that defines a model of the patient's knee.

In step 400, the surgical plan is computed. Said surgical plan can be automatically computed based on the target alignment parameter(s) given by the surgeon. Based on the target alignment parameter(s) and on the output(s) of the complex function, the control unit computes at least one correction parameter. Such a correction parameter generally corresponds to an amount of bone distraction or removal to achieve in order to obtain the desired alignment of the limb. More precisely, for each bone cut, the planning provides the geometry and the correction angle to be achieved.

In step 500, the surgical gesture is carried out. The osteotomy cut(s) is (are) done to achieve bone distraction or bone removal, depending on the type of correction decided by the surgeon. The surgeon may monitor in real time the progress of the surgical intervention, e.g. the evolution of the at least one correction parameter.

In step 600, which is optional, the surgeon may check the corrected alignment of the leg. At a fixed bone distraction position or bone closure position, updated measurement of the alignment parameter(s), in free or constraint position, can be displayed.

In step 700, the bone distraction or closure is fixed with a dedicated osteotomy implant when target alignment parameters are reached or when the surgeon decides the correction is achieved.

FIGS. 10A to 10E illustrate examples of a screen of the user interface at successive stages of the method.

FIG. 10A represents the screen in an initial step of the intraoperative procedure, comprising the entry of target alignment parameters in a region P of the screen (see step 100 of the flow chart of FIG. 9). In the illustrated example, two target alignment parameters P1, P2 are set, that can each be expressed as an angle (unit: °) or as a distance (unit: mm). Of course, only one target alignment parameter, or more than two target alignment parameters could be set. Besides, the target alignment parameter(s) can be expressed in any other suitable unit, such as % for example.

FIG. 10B represents the screen in a further stage of the intraoperative procedure, in which the position of the characteristic points in at least one constrained position of the leg has been determined and recorded by the control unit, and the complex function has been adjusted based on the knee measurement data set (see steps 200 and 300 in the flow chart of FIG. 9). The alignment parameters are displayed in a region A of the screen, distinct from the region P. In this way, the surgeon can see simultaneously the target alignment parameters and the measured alignment parameters. In the illustrated example, three alignment parameters A1, A2, A3 are displayed, that can each be expressed as an angle (unit: °) or as a distance (unit: mm). Of course, only one or two alignment parameters, or more than three alignment parameters could be computed and displayed. As mentioned above, the target alignment parameter(s) can be expressed in any other suitable unit, such as % for example. The screen can also comprise additional regions to display other information to guide acquisition of the position of the characteristic points in constrained position(s) of the leg. For example, a time slot allowed by the control unit to manipulate the leg can be displayed. Alternatively or additionally, a list of constrained positions to be achieved by the surgeon can be displayed.

FIG. 10C represents the screen in a further stage of the intraoperative procedure, in which the control unit has computed at least one correction parameter (corresponding to step 400 in the flow chart of FIG. 9). Such a correction parameter generally corresponds to an amount of bone distraction or removal to achieve in order to obtain the desired alignment of the limb. More precisely, for each bone cut, the planning provides the geometry and the correction angle to be achieved. The correction parameters are displayed in a region C of the screen, distinct from regions P and A. In this way, the surgeon can see simultaneously the target alignment parameters, the measured alignment parameters and the correction parameters. In the illustrated example, four correction parameters are displayed, two parameters $C_{coronal}$ and $C_{sagittal}$ expressed as angles (in °) and two parameters $C_3$, $C_4$ expressed as distances (in mm). Of course, additional and/or different correction parameters could be computed and displayed.

Advantageously, the volume of bone to be distracted or removed is computed by the control unit and displayed on the screen as a volume V that has a substantially wedge shape. The geometry of said volume V is correlated with the correction parameters; in particular, each correction parameter can be a geometric feature of the volume, such as a length of a side of the volume or an angle between two sides or faces of the volume. Generally, it is possible to establish a relationship between angles and distances. Thus, if the volume is defined by angle values, one can also define the volume by distance (e.g. length, width, height) values, and conversely.

Figure 10D:
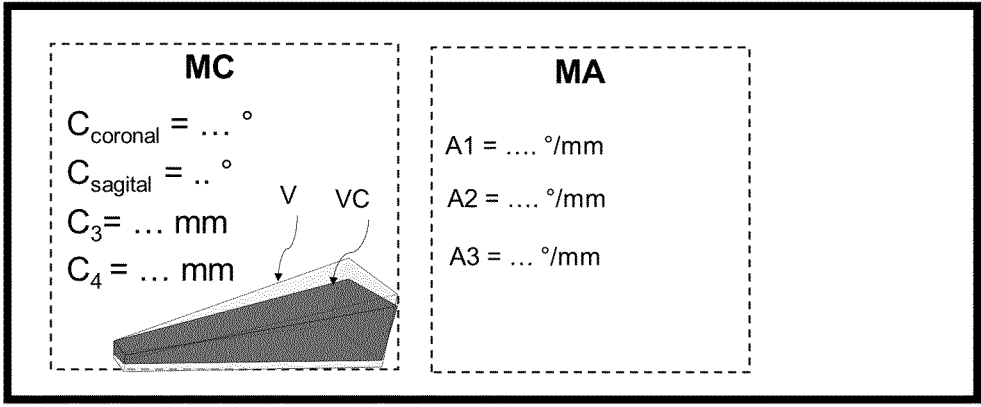

FIG. 10D represents the screen at a further stage of the intraoperative procedure, during the surgical gesture (see step 500 in the flow chart of FIG. 9). During the realization of the osteotomy cuts, bone distraction or bone removal, the surgeon may monitor in real time the progress of the surgical intervention, e.g. the evolution of the at least one correction parameter and the corresponding alignment parameters. In the illustrated example, the current correction parameters, as measured in real time, are displayed in a region MC of the screen, and the corresponding current alignment parameters are displayed in another region MA of the screen, distinct from the region MC.

Advantageously, the control unit also computes in real time the geometry of the volume of bone being distracted or removed, and displays it on the screen as a current volume VC superimposed with the target volume V. In this way, the surgeon can visualize easily a degree of progress of the opening or closing of the osteotomy.

Figure 10E:
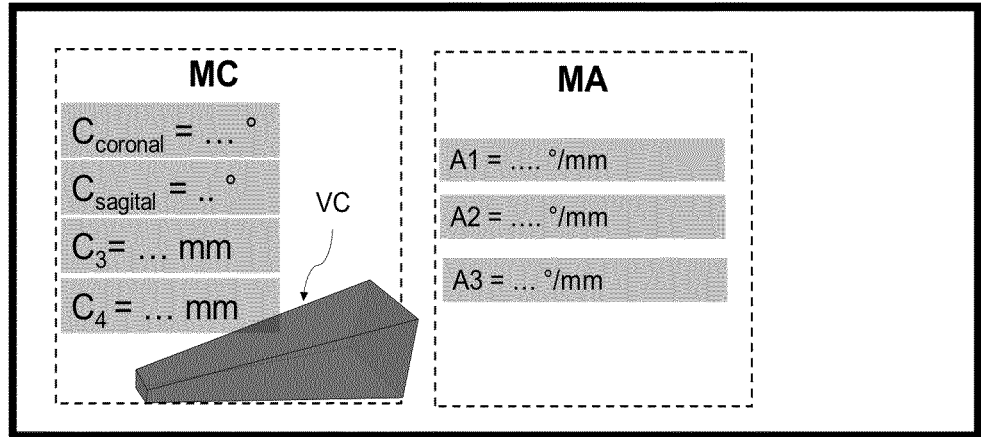

FIG. 10E represents the screen at the end of the surgical gesture, when the target alignment parameters have been achieved. In such situation, the control unit warns the surgeon by displaying the current correction parameters and alignment parameters with a specific color, e.g. green (schematically represented by the grey background) when they have reached the target value. Besides, the surgeon can observe that the current volume VC coincides with the target volume V.

Of course, the illustration of the screen in FIG. 10A to 10E is only given as an example and any other aesthetic or functional way of displaying information allowing the user to monitor the progress of the osteotomy procedure could be used without departing from the scope of the present disclosure.

As compared to the method of [Kim et al], the method described above allows computing correction parameters suited to the leg in the intraoperative position but taking into account laxities and influence of soft tissues thanks to the function defining a model of the patient's knee, and monitoring in real time the progress of the surgical gesture. In this way, a correct alignment of the leg can be achieved directly, without the need to rework the bone to adjust the correction and remedy to an over- or under-correction of the alignment.

REFERENCES

[Stulberg et al.] Stulberg S D, Yaffe M A, Shah R R, Gall-Sims S E, Palmese N, Granieri M A, Schmidt P H, Columbus primary total knee replacement: a 2-to 4-year followup of the use of intraoperative navigation-derived data to predict pre- and postoperative function, Orthopedics, 2008 October, Vol 31 (10 Suppl 1)

[Jud et al.] Jud L, Roth T, Fürnstahl P, Vlachopoulos L, Sutter R, Fucentese S F, The impact of limb loading and the measurement modality (2D versus 3D) on the measurement of the limb loading dependent lower extremity parameters, BMC Musculoskelet Disord, 2020 Jun. 30; 21 (1): 418.

[Kim et al.] Kim M S, Son J M, Koh I J, Bahk J H, In Y, Intraoperative adjustment of alignment under valgus stress reduces outliers in patients undergoing medial opening-wedge high tibial osteotomy, Archives of Orthopaedic and Trauma Surgery, 2017, 137 (8), 1035-1045

The invention claimed is:

1. A system for guiding an osteotomy procedure on at least one bone selected from a tibia and a femur pertaining to a patient's lower limb to correct a misalignment of said lower limb, said system comprising:

a control unit configured to be coupled to a localization system adapted to track a position and orientation of a tibial tracker fixed to the tibia and a femoral tracker fixed to the femur, wherein the control unit is configured to:

receive at least one target alignment parameter of the lower limb provided by a user;

determine a position of a set of characteristic points on at least one of the tibia and the femur relative to at least one of the tibial tracker and the femoral tracker;

track the positions of said characteristic points relative to the at least one of the tibial tracker and the femoral tracker based on localization data of the set of characteristic points during application of mechanical constraints by the user onto the patient's knee to simulate the effect of laxities and soft tissues onto the lower limb's alignment, said tracked positions forming a knee measurement data set;

based on the knee measurement data set, adjust a function defining a model of the patient's knee;

based on at least one output of said function and on at least one alignment parameter of the lower limb in the constrained position, determine at least one correction parameter of the osteotomy procedure to be applied to the lower limb to achieve the target alignment parameter.

2. The system of claim 1, wherein the knee measurement data set comprises at least one of: a set of ligament balance parameters, at least one laxity parameter and the at least one alignment parameter.

3. The system of claim 1, wherein the function is based on aggregation of patient data sets from intra-operative and post-operative alignment parameters of respective patients.

4. The system of claim 1, wherein the control unit is configured to modify the function based on machine learning methods to refine outputs of the function.

5. The system of claim 1, wherein the control unit is configured to monitor an evolution of the at least one alignment parameter based on localization data of the set of characteristic points during the osteotomy procedure.

6. The system of claim 1, wherein the control unit is further configured to determine, based on localization data of the set of characteristic points during the osteotomy procedure, whether each target alignment parameter is achieved.

7. The system of claim 1, wherein the control unit is further configured to monitor an evolution of a geometric feature of a volume being removed from or created in the bone by an osteotomy cut relative to the at least one correction parameter.

8. The system of claim 7, further comprising an additional tibial or femoral tracker configured to be fixed to the bone so that two tibial or femoral trackers are fixed to the bone on both sides of the osteotomy cut, wherein the control unit is configured to compute the evolution of the osteotomy cut based on localization data of said two trackers.

9. The system of claim 7, further comprising a mechanical device adapted to be inserted within the osteotomy cut and designed to expand or retract as the sides of the cut are moved farther or closer to each other, and at least one sensor coupled to the control unit and configured to measure in real time an expansion or a retraction of the mechanical device, wherein the control unit is configured to compute the evolution of the osteotomy cut based on measurement data from said at least one sensor.

10. The system of claim 7, further comprising two mechanical devices adapted to be fixed to sides of the osteotomy cut, an adjustable link connecting said mechanical devices and designed to expand or retract as the sides of the cut are moved farther or closer to each other, and at least one sensor coupled to the control unit and configured to measure in real time an expansion or a retraction of the adjustable link, wherein the control unit is configured to compute the evolution of the osteotomy cut based on measurement data from said at least one sensor.

11. The system of claim 1, further comprising a user interface coupled to the control unit, the user interface being configured to enter at least one user input, said user input comprising at least one of:

the at least one bone to be cut, an osteotomy type, such as an open-wedged osteotomy, a closed-wedge osteotomy or a more complex osteotomy, a number of cut to be made in each bone; and the at least one target alignment parameter.

12. The system of claim 11, wherein the user interface is configured to display at least one of: each of the at least one alignment parameter, each of the at least one correction parameter, and an indication that the at least one target alignment parameter is achieved.

13. The system of claim 1, wherein the at least one target alignment parameter comprises at least one of: a mechanical femorotibial angle (mFTA), a mechanical medial proximal tibial angle (mMPTA), a mechanical lateral distal femoral angle (mLDFA), a lateral tibial plateau inclination (LTPI), a medial tibial plateau inclination (MTPI), a hip-knee-ankle angle (HKA), a joint line convergence angle (JLCA), a posterior tibial slope (PTS), a hip abduction angle (HAA), a tibial plafond inclination (TPI), a talar inclination angle (TIA), a lateral patellar tilt (LPT) and a lateral patellar shift (LPS).

14. The system of claim 1, wherein the at least one correction parameter comprises a geometric feature of a bone part to be removed from the tibia or femur and a geometric feature of a space created around a hinge to appear during distraction of the tibia or femur.

15. The system of claim 1, wherein the control unit is further configured to determine the position of the set of characteristic points on the at least one of the tibia and the femur relative to the at least one of the tibial tracker and the femoral tracker based on at least one of:

a segmentation of at least one 2D or 3D medical image of the patient's limb and determining the set of reference characteristic points on said segmented image;

an adjustment of a bone model comprising the set of characteristic points to the patient's tibia or femur in at least one 2D or 3D image of the patient's limb using a bone morphing technique;

an obtention of localization data of a pointer tracker fixed to a pointer palpating characteristic points on the at least one of the tibia and the femur; and an obtention of localization data of the femoral and tibial trackers as a user moves the limb about at least one joint.

16. The system of claim 1, wherein the control unit is configured to be coupled to an X-ray imaging system adapted to acquire 2D or 3D images of the lower limb of the patient.

17. The system of claim 1, wherein the knee measurement data set relates to one position of the patient's leg without any constraint applied to the knee and one position of the patient's leg with mechanical constraints applied to the knee.

18. A method for guiding an osteotomy procedure on at least one bone selected from a tibia and a femur pertaining to a patient's lower limb to correct a misalignment of said lower limb, wherein a tibial tracker is fixed to the tibia and a femoral tracker is fixed to the femur and a localization system tracks a position and orientation of the tibial tracker and the femoral tracker, the method comprising:

receiving at least one target alignment parameter of the lower limb provided by a user;

determining a position of a set of characteristic points on at least one of the tibia and the femur relative to at least one of the tibial tracker and the femoral tracker;

applying mechanical constraints onto the patient's knee by a user to simulate effect of laxities and soft tissues onto the lower limb's alignment;

tracking positions of said characteristic points relative to at least one of the tibial tracker and the femoral tracker based on localization data of the set of characteristic points during application of said mechanical constraints, said tracked positions forming a knee measurement data set;

based on the knee measurement data set, adjusting a function defining a model of the patient's knee; and based on at least one output of said function and on the at least one alignment parameter of the lower limb in the constrained position, determining at least one correction parameter of the osteotomy procedure to be applied to the lower limb to achieve the target alignment parameter.

19. The method of claim 18, further comprising carrying out the osteotomy procedure, said osteotomy procedure comprising performing at least one osteotomy cut into the bone so as to form a hinge connecting two sides of the bone and moving said sides relative to each other around the hinge.

20. The method of claim 18, wherein the knee measurement data set comprises at least one of: a set of ligament balance parameters, at least one laxity parameter and at least one alignment parameter.

21. The method of claim 18, wherein the function is based on aggregation of patient data sets from intra-operative and post-operative alignment parameters of respective patients.

22. The method of claim 18, wherein the function is modified over time based on machine learning methods to refine outputs of the function.

23. The method of claim 18, further comprising monitoring an evolution of the at least one alignment parameter based on localization data of the set of characteristic points during the osteotomy procedure.

24. The method of claim 18, further comprising determining, based on localization data of the set of characteristic points during the osteotomy procedure, whether each target alignment parameter is achieved.

25. The method of claim 18, further comprising monitoring an evolution of a geometric feature of a volume being removed or created by the osteotomy cut relative to the at least one correction parameter.

26. The method of claim 18, further comprising:

fixing an additional tibial or femoral tracker to the bone so that two tibial or femoral trackers are fixed to the bone on both sides of the osteotomy cut; and computing an evolution of the osteotomy cut based on localization data of said two tibial or femoral trackers.

27. The method of claim 18, further comprising:

inserting a mechanical device into the osteotomy cut and expanding or retracting said mechanical device as the user moves the sides of the cut farther or closer to each other;

measuring in real time an expansion or a retraction of the mechanical device by at least one sensor; and computing an evolution of the osteotomy cut based on measurement data from said at least one sensor.

28. The method of claim 18, further comprising:

fixing two mechanical devices to both sides of the osteotomy cut, said mechanical devices being connected by an adjustable link;

expanding or retracting the adjustable link as a user moves the sides of the cut farther or closer to each other;

measuring in real time an expansion or a retraction of the adjustable link by at least one sensor; and computing an evolution of the osteotomy cut based on measurement data from said at least one sensor.

29. The method of claim 18, further comprising displaying, on a user interface, at least one of: each of the at least one alignment parameter each of the at least one correction parameter, and an indication that the at least one target alignment parameter is achieved.

30. The method of claim 18, wherein the at least one target alignment parameter comprises at least one of: a mechanical femorotibial angle (mFTA), a mechanical medial proximal tibial angle (mMPTA), a mechanical lateral distal femoral angle (mLDFA), a lateral tibial plateau inclination (LTPI), a medial tibial plateau inclination (MTPI), a hip-knee-ankle angle (HKA), a joint line convergence angle (JLCA), a posterior tibial slope (PTS), a hip abduction angle (HAA), a tibial plafond inclination (TPI), a talar inclination angle (TIA), a lateral patellar tilt (LPT) and a lateral patellar shift (LPS).

31. The method of claim 18, wherein the at least one correction parameter comprises a geometric feature of a bone part to be removed from the bone and a geometric feature of a space created around the hinge to appear during distraction of the bone sides.

32. The method of claim 18, wherein the position of the set of characteristic points on the at least one of the tibia and the femur relative to the at least one of the tibial tracker and the femoral tracker is determined based on at least one of the following methods:

segmenting at least one 2D or 3D medical image of the patient's limb and determining the set of reference characteristic points on said segmented image;

adjusting a bone model comprising the set of characteristic points to the patient's tibia or femur in at least one 2D or 3D image of the patient's limb using a bone morphing technique;

obtaining localization data of a pointer tracker fixed to a pointer palpating characteristic points on the at least one of the tibia and the femur; and obtaining localization data of the femoral and tibial trackers as a user moves the limb about at least one joint.

33. The method of claim 18, further comprising acquiring 2D images of the lower limb of the patient and determining the at least one target alignment parameter based on 2D X-ray images.

34. The method of claim 18, wherein the knee measurement data set relates to one position of the patient's leg without any constraint applied to the knee and one position of the patient's leg with mechanical constraints applied to the knee.

\* \* \* \* \*